(12) United States Patent
Graen (10) Patent No.: US 6,377,844 B1
(45) Date of Patent: Apr. 23, 2002

(54) R-WAVE DETECTOR CIRCUIT FOR SENSING CARDIAC SIGNALS

(76) Inventor: Dave Graen, 11440 Utah Ave. North, Champlin, MN (US) 55316

( * ) Notice: Subject to any disclaimer, the term of this patent is extended or adjusted under 35 U.S.C. 154(b) by 0 days.

(21) Appl. No.: 09/268,092

(22) Filed: Mar. 13, 1999

(51) Int. Cl.[7] .................................................. A61B 5/04
(52) U.S. Cl. ..................................................... 600/521
(58) Field of Search .................................. 600/508–528

(56) References Cited

U.S. PATENT DOCUMENTS

| 4,759,366 A | 7/1988 | Calaghan | 128/419 PG |
| 5,366,487 A | 11/1994 | Adams et al. | 607/5 |
| 5,458,621 A | 10/1995 | White et al. | 607/5 |
| 5,620,466 A | 4/1997 | Haefner et al. | 607/5 |
| 5,709,215 A | 1/1998 | Perttu et al. | 607/5 |
| 5,843,133 A | 12/1998 | Routh et al. | |
| 6,216,031 B1 * | 4/2001 | Findeis et al. | |

FOREIGN PATENT DOCUMENTS

EP 0 656 219 B1 7/1995 .......... A61N/1/365

OTHER PUBLICATIONS

Brumwell, et al. "The Amplifier: Sensing the Depolarization", *Implantable Cardioverter Defibrillator Therapy*, ed. Kroll and lehmann, Kluwer, p. 275–302, 1996.

* cited by examiner

*Primary Examiner*—Mark Bockelman
(74) *Attorney, Agent, or Firm*—Patterson, Thuente, Skaar & Christensen, P.A.

(57) ABSTRACT

Method and apparatus for measuring the heart rate in a human body. A first and second derivative of an electrical signal from the heart known as the QRS complex or R-wave is measured, and the values of the peak of the R-wave, the peak of the first derivative of the R-wave, and the peak of the second derivative of the R-wave are determined. The three peak values are then multiplied together to provide an output responsive to the occurrence of the R-wave which is greater than either the value of the peak of the R-wave, the value of the peak of the first derivative of the R-wave, or the value of the peak of the second derivative of the R-wave.

28 Claims, 9 Drawing Sheets

R-WAVE DETECTOR CIRCUIT FOR SENSING CARDIAC SIGNALS

FIELD OF THE INVENTION

The present invention relates to implantable cardiac stimulation devices, such as pacemakers, defibrillators and cardiaverters. More particularly, the present invention relates to an enhanced cardiac signal sensing system for sensing the occurrence of an R-wave.

BACKGROUND OF THE INVENTION

The field of implantable cardiac devices, such as pacemakers, defibrillators, and cardioverters, is well known. These devices typically monitor cardiac response under a variety of conditions. Sudden cardiac death presently claims an estimated 400,000 lives annually in the United States. To prevent sudden death, rapid treatment of cardiac conditions is required. Rapid treatment can be provided by implantable cardiac devices only if the heart rate can be accurately and reliably sensed. One potentially catastrophic cardiac event is fibrillation, wherein the heart ceases to function as a blood pump. Unless a functional heart rate is quickly reestablished, death can occur within minutes. Once the abnormal heart rate is sensed, a normal heart rate or sinus rhythm may be reestablished by application of a large electrical shock on the order of 10 joules or more, to defibrillate the heart.

Another serious condition is tachycardia or tachyrhythmia, which is a rapid heart rate which may eventually lead to fibrillation. Once the rapid heart rate is sensed, a normal heart rate or sinus rhythm may be reestablished by application of a slightly more rapid rate of very low level pacing shocks of less than 100 micro joules to capture the heart rate and slow the heart to a normal rate. The normal sinus rhythm may also be reestablished by application of electrical shocks on the order of 1 joule to perform cardioversion on the heart.

The necessity of identifying persons likely to suffer tachyrhythmia or fibrillation has led to the preventative step of implanting a device known as an Implanted Cardioverter Defibrillation (ICD) device. The ICD device is electrically attached to the patient's heart. Rather than relying on the patient or on attending medical personnel to identify a cardiac fibrillation event, the ICD device uses automatic triggering. With automatic triggering, accurate monitoring and detection of the heart rate is required to detect the cardiac fibrillation event and trigger the ICD device to defibrillate the heart.

Monitoring and detection of cardiac function typically involves electrical sensing of muscle and nerve cell depolarizations which can be correlated with cardiac muscle contractions. Electrodes are implanted in the heart which sense an electrical voltage which is measured over time to produce an electrocardiogram wave form. The electrocardiogram wave form under normal conditions includes a P wave, followed by a complex three-part wave form called the QRS complex, and then a T wave. Of these various components, the QRS complex or R-wave has a dominant amplitude feature and is therefore most typically used to sense the heart rate. The R-wave is the portion of the electrocardiogram wave form having the steepest slopes and the sharpest peaks. The heart rate is the interval between R-waves, and is sometimes termed the R—R interval. R-waves typically have a peak amplitude in the range of about 5 to 15 mv during a normal sinus rhythm. T waves typically have a peak amplitude of about half of the R-wave amplitude. Noise and extraneous muscle movements typically have peak amplitudes in the range of about 0.1–1 mv. During fibrillation, the R-wave amplitude may diminish to as little as 20% of normal amplitude (e.g., 1.0 to 3.0 mv), thus making the R-wave amplitude indistinguishable from noise levels.

In one approach, detection systems sense the occurrence of R-wave electrical events and signals exceeding a preset constant voltage, where the constant voltage is fixed at a preset amplitude between 3.4 to 10 mv. Such triggering levels start at approximately 67% of the amplitude of a normal R-wave, which is higher than typical noise or T-wave amplitudes. During fibrillation, the R-wave amplitudes decrease to a range of 0.5 to 2.0 mv. Unfortunately, this type of prior art detection system having the preset and fixed amplitude detection threshold is incapable of distinguishing or sensing diminished or degenerating R-wave events during fibrillation. With this approach, R-wave information on heart rate is completely unreliable during fibrillation.

More recently, detection systems have attempted to address the problem of sensing diminishing R-wave amplitudes during fibrillation by employing a sensitivity threshold which starts at a preset amplitude and then subsequently becomes more sensitive until a floor threshold is reached. The preset amplitude is typically 67% of the preceding R-wave amplitude, and the floor threshold is typically set at 0.3 to 0.5 mv. This floor threshold prevents the sensitivity threshold from dropping to such low levels that the increased sensitivity begins to incorrectly detect noise as R-waves. This reduction in threshold amplitude and increase in sensitivity occurs in the form of an exponential decay with a time constant on the order of 1 to 1.5 seconds. This time constant is reset after each R-wave event. In one example, the "SENTINEL"™ brand ICD device, developed by Angeion Corporation, employs a detection mechanism in which the initial threshold is a preset percentage of the most recent R-wave peak amplitude, and the decay is a standard exponential. The threshold used in the "SENTINEL"™ device is lowered from the initial level until a constant floor threshold is reached. In another example, an initial threshold reset may be used which decays with a reverse exponential time constant to the floor threshold, where the floor threshold is set to a constant level which is greater than the noise level.

One problem with these approaches is temporary supersensitivity when a low amplitude R-wave occurs during normal sinus rhythm or tachycardia. This problem results from the decay being based upon a fixed time constant, or from the detection mechanisms resetting the initial threshold after each R-wave detection. Once the detection mechanisms observe a low amplitude R-wave, for example, of less than 3 mv, the initial sensitivity threshold is set to a low level of about 2 mv or less, and then proceeds to decline to the floor level of about 0.3 to 0.5 mv. At this level, the sensitivity threshold may allow noise to be falsely detected as R-waves. This problem is particularly severe in situations where the floor threshold is quite sensitive (e.g., when the floor setting is 0.4 mv and the noise level is 0.5 or 0.6 mv). This incorrect or false detection of noise as R-waves resets the initial threshold sensitivity to inappropriately low levels resulting in possible adverse effects to the patient. These adverse effects may include the initiation of electrical shock therapy to the heart based upon noise timing rather than R-wave timing. The electrical shock therapy would continue until a true R-wave was detected and the system could correct itself.

More recently, in another approach, an ICD detection method for sensing the occurrence of an R-wave attempts to distinguish R-waves from noise through the use of variable declining sensitivity thresholds. This approach, disclosed in U.S. Pat. No. 5,709,215 and developed by Angeion Corporation, considers the amplitude of at least the previous most recent R-wave, and determines a declining threshold of sensitivity which is used to recognize a subsequent electrical signal as an R-wave. With this approach, the amplitude of the previous R-wave may be classified, based on amplitude. Based upon the classification, a desirable time constant for the declining threshold of sensitivity is provided as either an exponential or a reverse exponential decay. Alternatively, piece wise use of various decay formulas may be combined and used.

This approach, while an improvement over previous approaches, is still dependent solely upon R-wave amplitude, and requires the setting of an appropriate sensitivity threshold to recognize the occurrence of an R-wave. Furthermore, this approach is still dependent upon distinguishing R-wave signal amplitudes from noise level amplitudes, and thus requires the R-wave to have a greater amplitude than the noise level amplitude, in order to avoid false recognition of noise as R-waves.

SUMMARY OF THE INVENTION

An R-wave detection method and apparatus for sensing the occurrence of an R-wave by utilizing characteristics of the R-wave which distinguish the R-wave from other portions of the electrocardiogram waveform is disclosed. With this approach, a first and second derivative is taken from an electrical signal measured from the heart. The electrical signal, known as the QRS complex or R-wave, is unique from other portions of the electrocardiogram waveform in that the product of the maximum value of the amplitude of the R-wave, the maximum value of the first derivative or slope of the R-wave, and the maximum value of the second derivative or slope transition of the R-wave, is greater for the R-wave than for any other portion of the electrocardiogram waveform. Once the values of the peak of the R-wave, the peak of the first derivative of the R-wave, and the peak of the second derivative of the R-wave are determined, the three peak values are multiplied together to provide an output product value. The output product value is greater in amplitude than either the value of the peak of the R-wave, the value of the peak of the first derivative of the R-wave, or the value of the peak of the second derivative of the R-wave , and is also higher than any other portion of the electrocardiogram waveform including background noise.

In a preferred embodiment of the present invention, an R-wave detector is provided to measure the heart rate from a tip-ring signal provided from sensing electrodes implanted in the heart. The tip-ring signal is an electrical voltage signal which is provided to a buffer which may optionally perform signal preconditioning. This signal preconditioning may include filtering or automatic gain control to bring the signal amplitude up to or down to any desired level. The output of the buffer is provided to a first self-clearing peak detector which provides an output proportional to the peak of the electrical signal, which is also the zeroth derivative of the electrical signal. The output of the buffer is also provided to two cascade differentiators which determine the first and second derivatives of the electrical signal. The output of the first differentiator is provided to a second self-clearing peak detector which provides an output proportional to the peak of the first derivative of the electrical input signal. The output of the second differentiator is provided to a third self-clearing peak detector which provides an output proportional to the peak of the second derivative of the electrical signal. The peak detectors are self-clearing as they maintain the output for a predetermined time before clearing. The outputs of the first, second and third self-clearing peak detectors are provided to a multiplier which multiplies the outputs together to provide a product output. The multiplier product output is proportional to the product of the peaks of the zeroth, first and second derivative of the electrical input wave form. The multiplier product output is provided to a self-clearing fraction of peak detector which provides an output response once the product output from the multiplier is received. The self-clearing fraction of peak detector may optionally couple to a one-shot device which provides a digital pulse output having Complimentary Metal Oxide Semiconductor (CMOS) voltage levels.

In an alternative embodiment of the present invention, self-clearing peak to peak detectors are used rather than peak detectors to provide a greater amplitude output to the multiplier. In the alternative embodiment, the outputs of the buffer, first differentiator and second differentiator provide the zeroth, first and second derivatives respectively of the input electrical signal wave form to the first self-clearing peak to peak detector, the second self-clearing peak to peak detector and the third self-clearing peak to peak detector. The zeroth, first and second derivative have both positive and negative peaks which are inherent in the R-wave signal, and which may be measured by the self-clearing peak to peak detector. The self-clearing peak to peak detectors provide an output proportional to the sum of the peak positive amplitude and the inverted peak negative amplitude of the input signal. Since this sum is greater than either the positive or negative peak alone, a higher level output response from the self-clearing peak to peak detector is provided to the multiplier, thus improving the ability to detect low amplitude electrical signals measured from the heart.

In another alternative embodiment of the present invention, a buffer is provided to receive the electrical input signal measured from the heart, and perform any desired signal conditioning before coupling the electrical input signal to a self-clearing peak to peak detector and an input of a comparator. The self-clearing peak to peak detector output couples to a resistor divider network, and an output of the resistor divider network couples to the other input of the comparator. The comparator compares the output of the resistor divider network, which is a fraction of the peak to peak value of the electrical input signal, to the electrical input signal, and provides an output when the R-wave is detected. Since the self-clearing peak to peak detector provides an output proportional to the sum of the peak positive amplitude and the inverted peak negative amplitude of the detected R-wave, which is greater than the positive or negative peak of the R-wave signal provided from the buffer, the R-wave can be easily detected by the comparator. The output of the comparator may optionally couple to a one-shot device which provides a digital pulse output having CMOS voltage levels.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
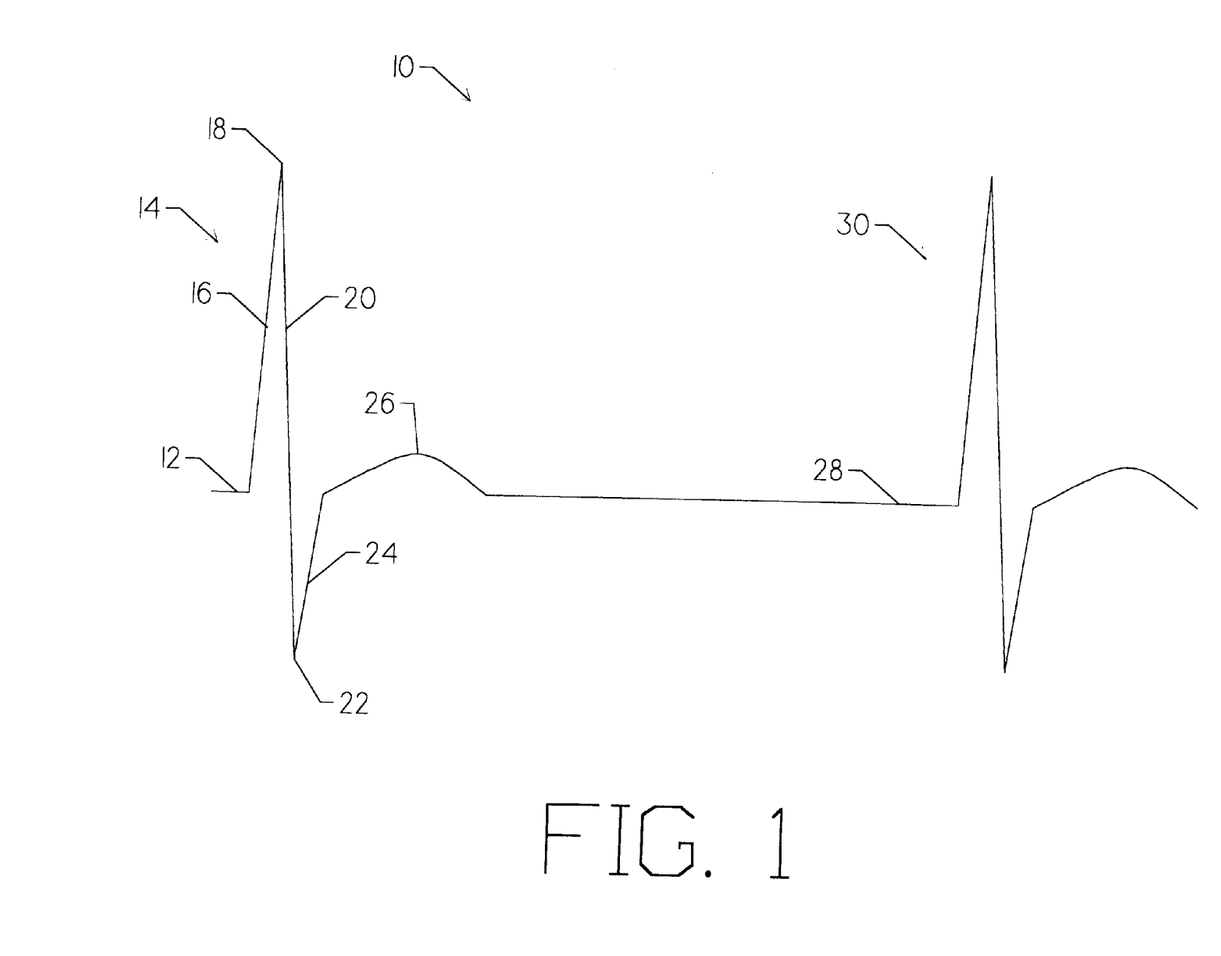
FIG. 1 is a graphical representation of a heart rate electrical signal over time showing the R-wave.

FIG. 1 is a graphical representation of a heart rate electrical signal over time showing the R-wave. The electrical signal is shown generally at 10, and illustrates R-waves occurring at 14 and 30. The electrical signal 10 is typically generated from sensing electrodes implanted in the heart, and is shown being displayed on the ordinate and plotted over the course of time, along the abscissa. R-waves have typical peak amplitudes in the range of 5–15 mv during normal sinus rhythm. The peak of R-wave 14 is indicated at 18.

R-waves have several attributes which are unique. R-waves generally have steeper transitional slopes (indicated at 16 and 20), and higher peak amplitudes (indicated at 18), than other portions of the electrocardiogram waveform. The product of the peak amplitude of the R-wave, indicated at 18, the peak value of the slopes or first derivative of the R-wave, indicated at 16 and 20, and the peak value of the slope transition or second derivative of the R-wave, indicated at 18, is greater for the R-wave than for any other portion of the electrocardiogram waveform.

The R-wave shown in 14 further has a negative peak amplitude indicated at 22, and has a third slope indicated at 24, which returns to the beginning of a T-wave shown at 26. The peak to peak amplitude of the R-wave is measured between the peak at 18 and the peak at 22. The peak to peak value of the first derivative of the R-wave is equal to the addition of positive values of the peak positive first derivative and peak negative first derivative measured at 16, 20 and 24. The peak to peak value of the second derivative of the R-wave is equal to the addition of positive values of the peak positive second derivative and peak negative second derivative measured at 18 and 22. The product of the peak to peak amplitude of the R-wave, the peak to peak value of the first derivative of the R-wave, and the peak to peak value of the second derivative of the R-wave, is greater for the R-wave than for any other portion of the electrocardiogram waveform.

Figure 2:
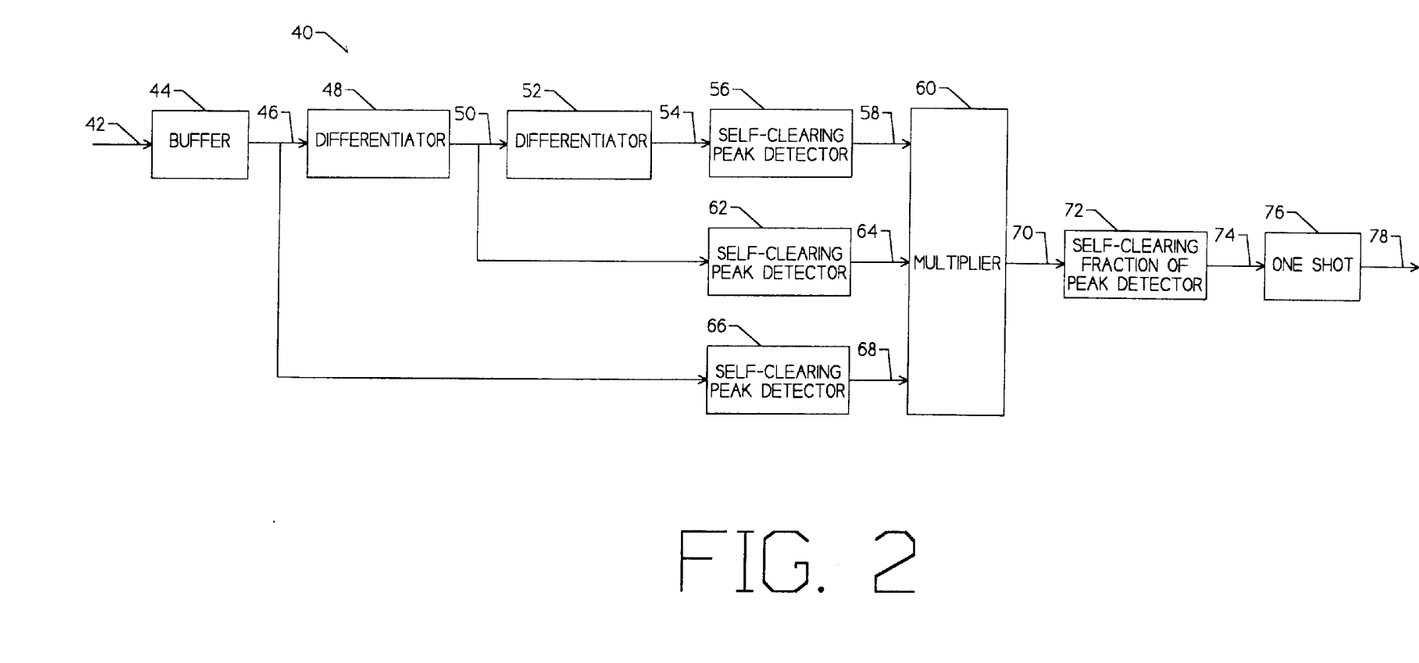
FIG. 2 is a block diagram showing the preferred embodiment of the present invention.

FIG. 2 is a block diagram showing a preferred embodiment of the present invention. FIG. 2 shows an R-wave detector which differentiates the QRS complex or R-wave from electrical signal 10 by using attributes other than R-wave amplitude. The R-wave generally has several attributes unique in the overall waveform, including the highest amplitude, the steepest slopes or first derivatives, and the sharpest peaks or second derivatives, all occurring within a short period of time. While other portions of electrical signal 10 may occasionally be greater, only the R-wave has the near simultaneous occurrence of a high number of these attributes. The R-wave detector shown generally at 40 thus detects the R-wave as the signal having the highest amplitude, first and second derivatives occurring nearly simultaneously.

With the R-wave detector shown at 40, electrical signal 10 is input to buffer 44 via interface 42. The input at 42 may be the tip-ring signal from a lead, such as a typical intra cardiac bipolar electrode, to sense the waveform or electrical signal 10 generated by the passage of a depolarization wave through a region of the heart. Buffer 44 is optional in the preferred embodiment and may be used to perform any required signal conditioning or filtering. The filtering may be used to remove noise in the signal. Buffer 44 may also perform preconditioning such as automatic gain control to bring the amplitude of electrical signal 10 up or down to a desired level.

The output of buffer 44 couples to differentiator 48 and self-clearing peak detector 66 via interface 46. Differentiator 48 and differentiator 52 perform as two cascade differentiators to provide a first and second derivative of the buffer 44 output. The output of buffer 44 at interface 46 is the zeroth derivative, while the output of differentiator 48 at interface 50 is the first derivative, and the output of differentiator 52 at interface 54 is the second derivative. The output of buffer 44 is directly proportional to the peak of R-wave 14, shown at 18 in FIG. 1. The output of differentiator 48 is proportional to the slope or first derivative of R-wave 14, while the output of differentiator 52 is proportional to the second derivative of R-wave 14.

The outputs of differentiator 52 at interface 54, differentiator 48 at interface 50 and buffer 44 at interface 46, are input to self-clearing peak detector 56, self-clearing peak detector 62 and self-clearing peak detector 66, respectively. The outputs of buffer 44, differentiator 48 and differentiator 52 are nearly instantaneous, and depend only on the band width, slew rate or phase delay of the particular operational amplifiers used. The self-clearing peak detectors are used to look for high values of the zeroth, first and second derivatives obtained from electrical signal 10. Self-clearing peak detectors 56, 62 and 66 look for high values of the outputs of differentiator 52, differentiator 48 and buffer 44, respectively, and provide an output proportional to the high value for a predetermined time until clearing. The delay until clearing or resetting of the outputs of self-clearing peak detectors 56, 62 and 66 can be preset depending on how much delay is needed. For example, the delay in electrical signal 10 may determined by the time delay between the beginning upward transition of slope 16 of R-wave 14, and the end of the negative going transition at 20 for R-wave 14.

The outputs of self-clearing peak detector 56, self-clearing peak detector 62 and self-clearing peak detector 66 are input to multiplier 60 via interfaces 58, 64 and 68, respectively. Multiplier 60 performs a multiply or logical AND function on the input signals. Multiplier 60 provides an output which is proportional to the product of the inputs at interface 70.

Self-clearing fraction of peak detector 72 has an input at interface 70 and an output at interface 74. Self-clearing fraction of peak detector 72 can be set to detect any desired output level or threshold of multiplier 60 at interface 70, and provide an output at interface 74. Self-clearing fraction of peak detector 72 is coupled to one shot 76 via interface 74.

One shot 76 may optionally be used to provide a digital pulse output at interface 78 where the digital pulse output has Complimentary Metal Oxide Semiconductor (CMOS) voltage levels.

Figure 3:
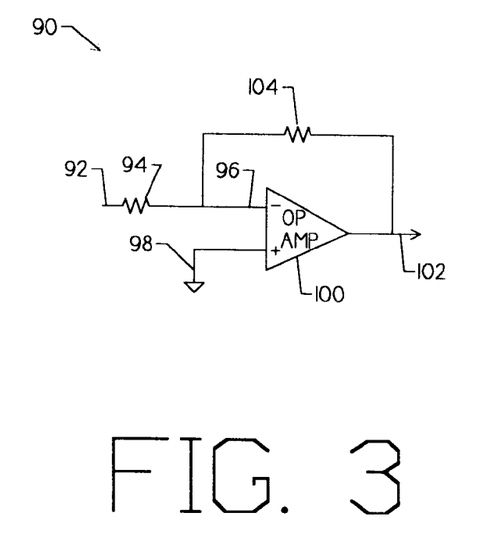
FIG. 3 is a schematic diagram showing the input buffer of FIG. 2.

FIG. 3 is a schematic diagram of the input buffer of FIG. 2. The input buffer is shown generally at 90, and is buffer 44 of FIG. 2. Input buffer 90 has an input at interface 92. Interface 92 corresponds to interface 42 of FIG. 2. Input buffer 90 has an output at interface 102. Interface 102 corresponds to interface 46 of FIG. 2. Operational amplifier 100 may be any number of operational amplifiers well known in the art. For example, operational amplifier 100 may be a Harris 4741 Quad Operational Amplifier, a National LF 347 Quad Operational Amplifier, or a National LM 348 Quad Operational Amplifier. Operational amplifier 100 has a positive input which is tied to ground through interface 98. The negative input of operational amplifier 100 is coupled to resistor 94 via interface 96. Resistor 94 also is coupled to interface 92.

It is appreciated by those skilled in the art that input buffer 90 may perform any number of functions including amplification of an input at interface 92, or provide a positive or negative gain to the input at interface 92. Furthermore, it is appreciated that the values of the resistors and capacitors utilized within input buffer 90 are well known in the art, and may be dependent upon the particular manufacturers operational amplifier used, as well as the specific function being performed.

Figure 4:
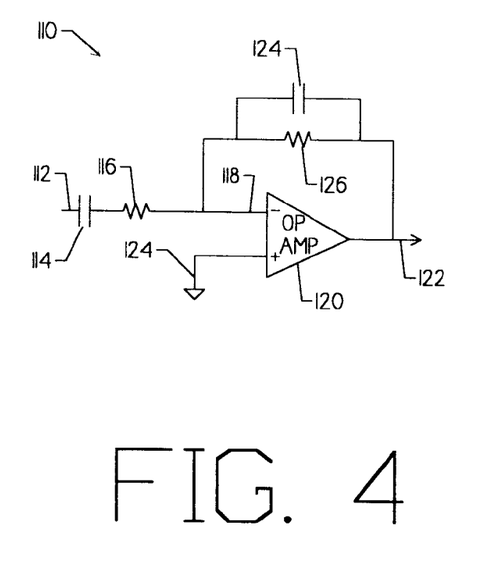
FIG. 4 is a schematic diagram showing the differentiator of FIG. 2.

FIG. 4 is a schematic diagram showing the differentiator of FIG. 2. The differentiator is shown generally at 110, and is the circuit diagram for either differentiator 48 or differentiator 52 in FIG. 2. The input to differentiator 110 is at interface 112. Operational amplifier 120 is equivalent to operational amplifier 100 discussed in FIG. 3. Capacitor 114 and resistor 116 are coupled in series between interface 112 and the negative input of operational amplifier 120 at interface 118. Capacitor 124 and resistor 126 are coupled in parallel between interface 118 and the output of operational amplifier 120 at interface 122. The positive input of operational amplifier 120 is coupled to ground via interface 124. It is appreciated that the values of the resistors and capacitors utilized within differentiator 110 are well known in the art, and may be dependent upon the particular manufacturers operational amplifier used.

Figure 5:
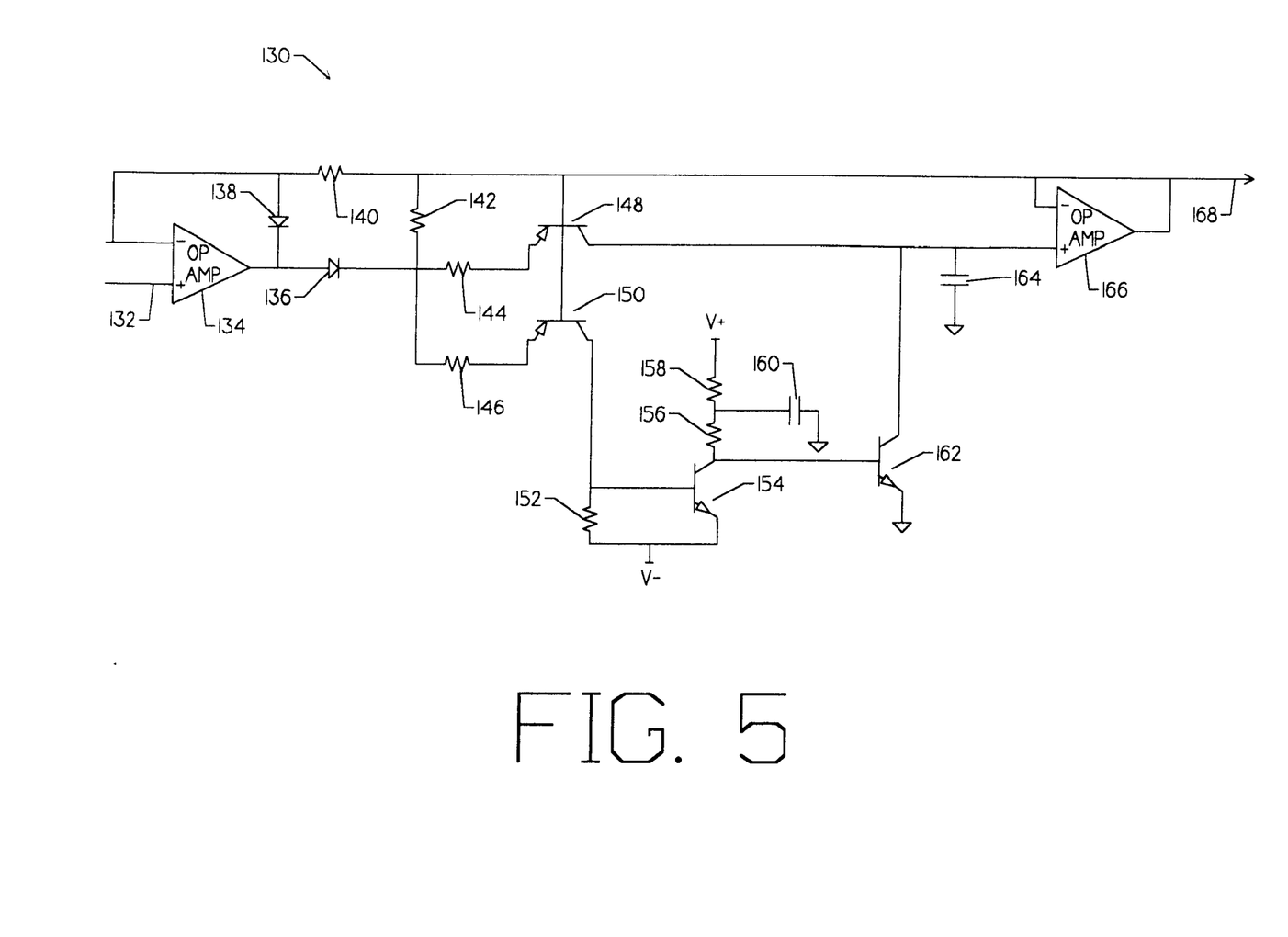
FIG. 5 is a schematic diagram showing the self-clearing peak detector of FIG. 2.

FIG. 5 is a schematic diagram showing the self-clearing peak detector of FIG. 2. The self-clearing peak detector is shown generally at 130, and is representative of self-clearing peak detector 56, self-clearing peak detector 62 or self-clearing peak detector 66 shown in FIG. 2. Self-clearing peak detector 130 provides an output at interface 168 which is proportional to the peak input level at interface 132. Self-clearing peak detector 130 also provides the level representing detection of the peak for a period of time before clearing. This period of time is at least as great as the time response of electrical signal 10 of FIG. 1 between positive slope 16 and negative slope 20. The time delay must also account for any inherent delay occurring through buffer 44, differentiator 48 and differentiator 52, to provide multiplier 60 with enough time to perform the multiplication. Once each output of self-clearing peak detector 56, 62 and 66 are held respectively at interfaces 58, 64 and 68, multiplier 60 can output a product of the three inputs at interface 70. After the predetermined time delay, the output of self-clearing peak detector 130 returns to a pre-peak detection level. In the preferred embodiment, this level is zero volts.

The input section of self-clearing peak detector 130 consists of operational amplifier 134 coupled to an anode of diode 136 and a cathode of diode 138. Resistors 140 and 142 are coupled in series across diodes 136 and 138. The connection between resistors 140 and 142 is coupled to the output of self-clearing peak detector 130 at interface 168. The connection between diode 136 and resistor 142 is coupled to the emitter of transistor 148 through resistor 144, and the emitter of transistor 150 through resistor 146. The base of transistors 148 and 150 are coupled to the output of self-clearing peak detector 130 at interface 168. The collector of transistor 148 is coupled to the positive input of operational amplifier 166, while the negative input of operational amplifier 166 is coupled to interface 168. The output of operational amplifier 166 is also coupled to interface 168.

The time delay and peak detection function of self-clearing peak detector 130 is performed as follows. The collector of transistor 150 is coupled through resistor 152 to a V-voltage supply, which has a negative potential. The collector of transistor 150 also couples to the base of transistor 154, and the emitter of transistor 154 couples to the V-voltage supply. The delay time constant is set by the values of resistor 156, resistor 158, and capacitor 160. The peak value sensed by self-clearing peak detector 130 is stored in capacitor 164, which is coupled to the positive input of operational amplifier 166. It is understood that once the time constant of resistor 156, resistor 158 and capacitor 160 has expired, transistor 162 turns on and shorts capacitor 164 to a near ground potential, to reset self-clearing peak detector 130.

Figure 6:
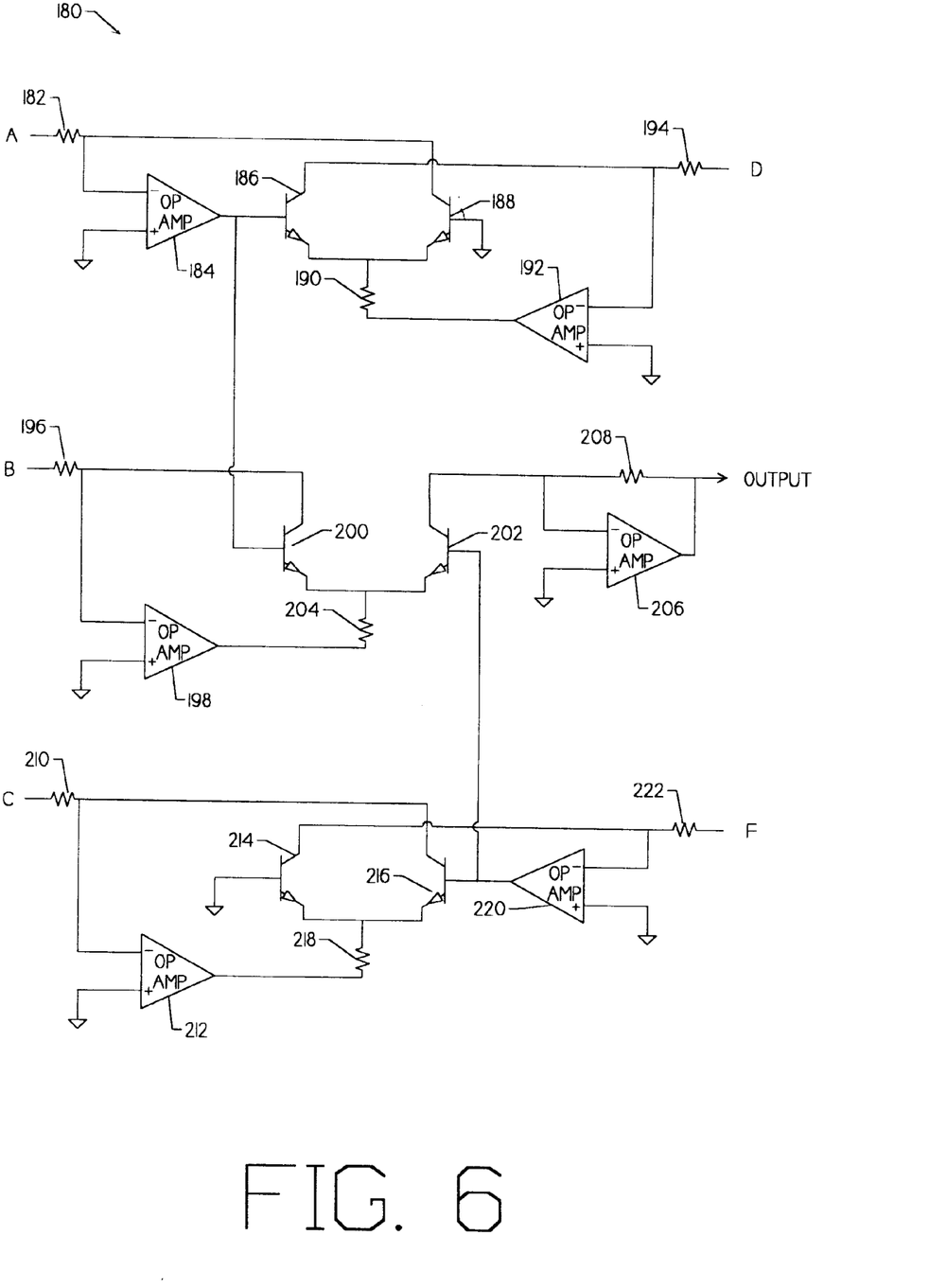
FIG. 6 is a schematic diagram showing the multiplier of FIG. 2.

FIG. 6 is a schematic diagram showing multiplier 60 of FIG. 2. The multiplier is shown generally at 180. Multiplier 180 has inputs at A, B, and C which correspond respectively to interfaces 58, 64 and 68 of multiplier 60 in FIG. 2. Multiplier 180 has an output labeled OUTPUT, which corresponds to interface 70 of multiplier 60 in FIG. 2. The inputs at D and F are tied to a reference potential. Operational amplifiers 184 and 192, resistors 182, 190 and 194, and transistors 186 and 188 provide the functionality for input A. Operational amplifiers 198 and 206, resistors 196, 204 and 208, and transistors 200 and 202 provide the functionality for input B, and also provide the product output at the OUTPUT interface. Operational amplifiers 212 and 220, resistors 210, 218 and 222, and transistors 214 and 216 provide the functionality for the C input. Multiplier 180 is a one-quadrant log-antilog multiplier, where the three numerator input are A, B and C, and the three denominator inputs are D, OUTPUT and E. In operation, once the peak values of the zeroth, first and second derivatives are received at inputs at A, B and C, multiplier 180 performs a multiplication and provides a product output at the OUTPUT terminal, where the product output is proportional to the product of the inputs at A, B, and C.

Figure 7:
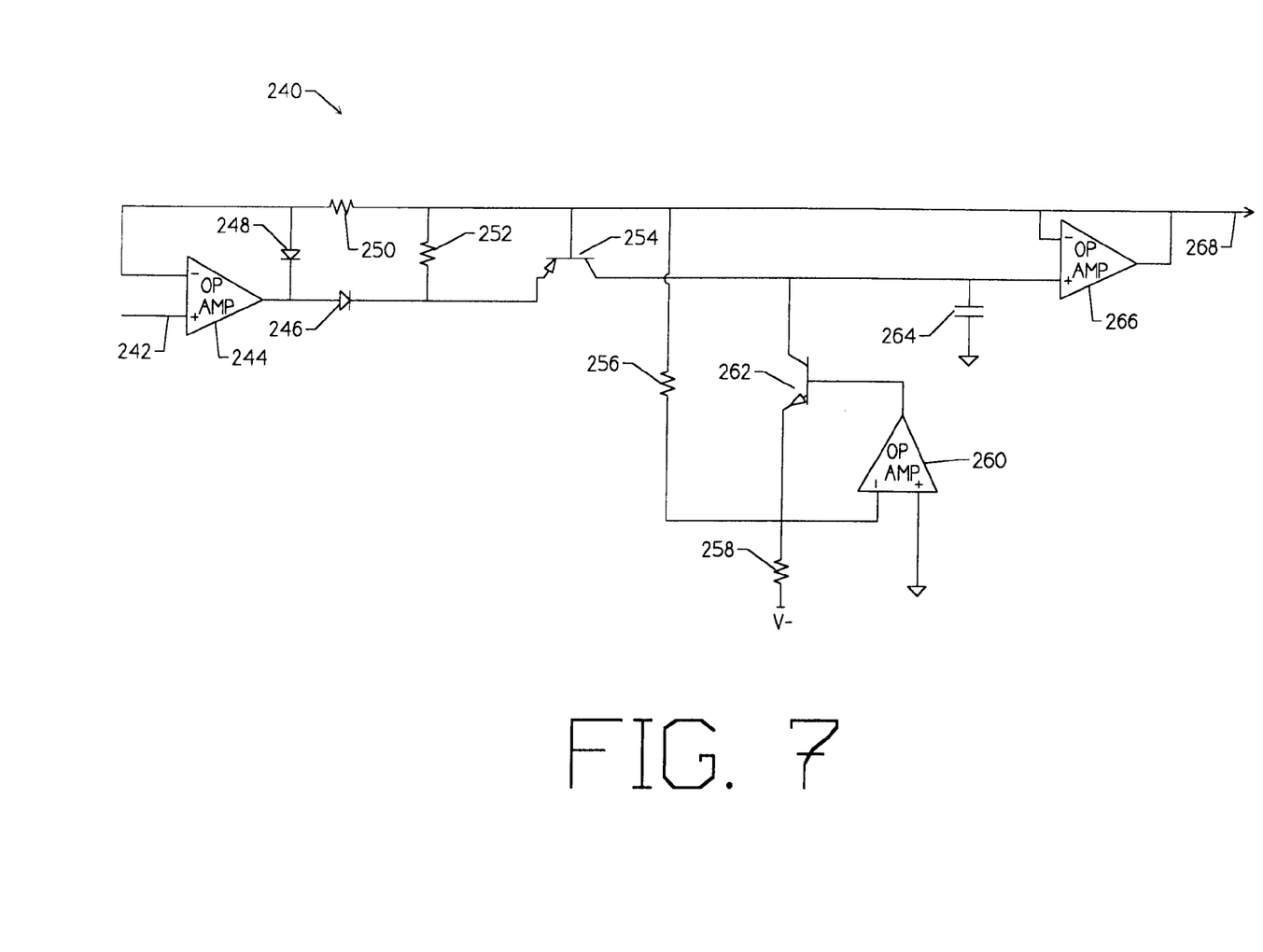
FIG. 7 is a schematic diagram showing the self-clearing fraction of peak detector of FIG. 2.

FIG. 7 is a schematic diagram showing the self-clearing fraction of peak detector of FIG. 2. The self-clearing fraction of peak detector is shown generally at 240 and has an input at interface 242 which correspond to interface 70 of FIG. 2, and an output at interface 268 which corresponds to interface 74 of FIG. 2. Self-clearing fraction of peak detector 240 has an input section comprised of operational amplifier 244, diodes 246 and 248, resistors 250 and 252, and transistor 254. The output of operational amplifier 266 at interface 268 couples back to resistors 250 and 252 and provides a base input to transistor 254. The emitter of transistor 254 is coupled to diode 246 and resistor 252, and the collector of transistor 254 is coupled to the positive input of operational amplifier 266. The negative input of operational amplifier 266 is coupled to interface 268. Capacitor 264 couples between the positive input of operational amplifier 266 and a ground potential to perform a charge storage function to store the fraction of peak detection level for a predetermined period.

The fraction of the peak input at interface 242 which is detected is set by the ratio of resistors 256 and 258. Resistors 256 and 258 comprise a voltage divider which couples between the output of self-clearing fraction of peak detector 240 at interface 268 and a V- potential. The voltage divider connection point between resistors 256 and 258 couples to both the minus input of operational amplifier 260 and the emitter of transistor 262. Operational amplifier 260 has a positive input which is coupled to ground and has an output coupled to the base of transistor 262. Operational amplifier 260 performs the self clearing function after the predetermined period by turning on transistor 262 to discharge the charge stored across capacitor 264.

Figure 8:
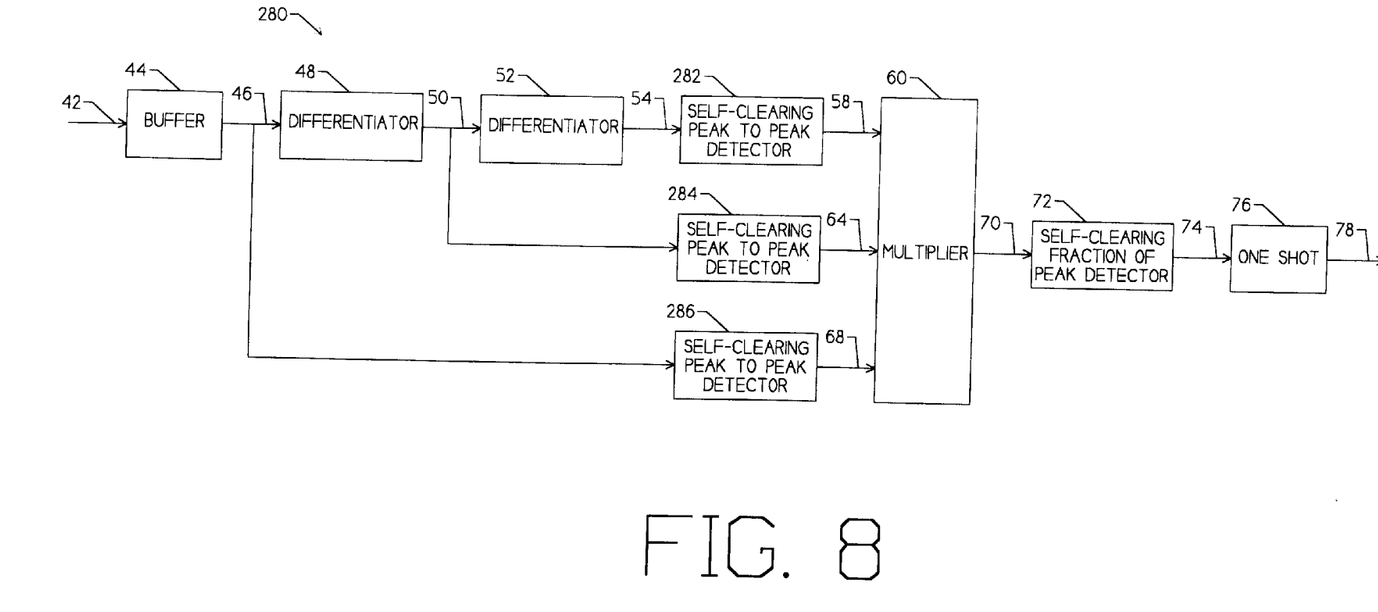
FIG. 8 is a block diagram showing an alternative embodiment of the present invention.

FIG. 8 is a block diagram showing an alternative embodiment of the present invention. In the alternative embodiment, shown generally at 280, self-clearing peak to peak detector 282, self-clearing peak to peak detector 284, and self-clearing peak to peak detector 286 replace self-clearing peak detector 56, self-clearing peak detector 62 and self-clearing peak detector 66, respectively, as shown in FIG. 2. The self-clearing peak to peak detector provides additional signal sensing capability by providing an output which is proportional to the peak to peak value of the input voltage, not just the peak value as with the self-clearing peak detector shown in FIG. 5.

Self-clearing peak to peak detector 286 is coupled to the output of buffer 44 and provides an output proportional to the difference between the positive peak of R-wave 14 at 18, and the negative peak of R-wave 14 at 22 (see also, FIG. 1). Self-clearing peak to peak detector 284 is coupled to the output of differentiator 48 and provides an output proportional to the sum of the peak positive amplitude and the inverted peak negative amplitude of the first derivative output from differentiator 48. The first derivative is maximized for R-wave 14 at the positive and negative slopes shown at 16, 20 and 24 in FIG. 1. Self-clearing peak to peak detector 282 is coupled to the output of differentiator 52 and provides an output proportional to the sum of the peak positive slope transition and the inverted peak negative slope transition of the second derivative output from differentiator 52. The second derivative is maximized for R-wave 14 at the peak positive and negative slope transitions shown at 18 and 22 in FIG. 1.

Figure 9:
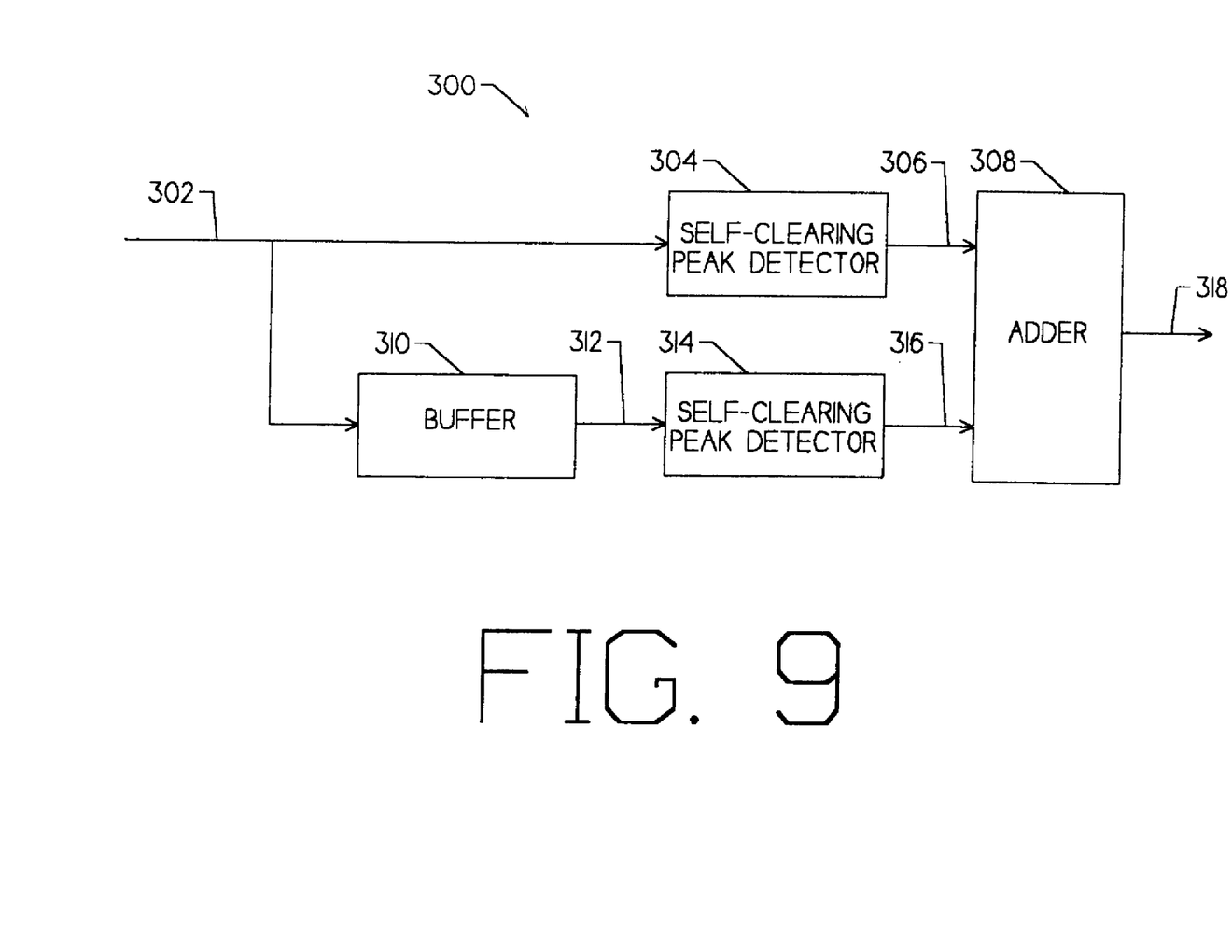
FIG. 9 is a block diagram showing the self-clearing peak to peak detector of FIG. 8.

FIG. 9 is a block diagram showing the self-clearing peak to peak detector of FIG. 8. The self-clearing peak to peak detector is shown generally at 300, and is representative of self-clearing peak to peak detector 282, 284 or 286, as shown in FIG. 8. The input to self-clearing peak to peak detector 300 is at interface 302, and the output is at interface 318. The input at 302 is coupled to buffer 310, which is a unity gain buffer similar to buffer 44 shown in FIG. 8. Buffer 310 also performs an inversion function to invert the signal input at interface 302, and provides the inverted signal at interface 312 to self-clearing peak detector 314. Self-clearing peak detector 304 is coupled to the input at interface 302. Self-clearing peak detector 130 shown in FIG. 5 is representative of self-clearing peak detector 304 and self-clearing peak detector 314.

Self-clearing peak detector 304 or 314 can sense either positive or negative going peaks. With the proper inversion provided by buffer 310, the peak to peak detection function can be accomplished. With the self-clearing peak to peak detector 300, self-clearing peak detector 304 and 314 detect positive going peaks. Since buffer 310 inverts the input provided at interface 302, self-clearing peak detector 304 provides an output responsive to the positive going peak at 302, and self-clearing peak detector 314 provides an output responsive to the negative going peaks at interface 302. Adder 308 is coupled to self-clearing peak detector 304 via interface 306, and self-clearing peak detector 314 via interface 316. Adder 308 sums these two inputs and provides a sum output at 318.

Figure 10:
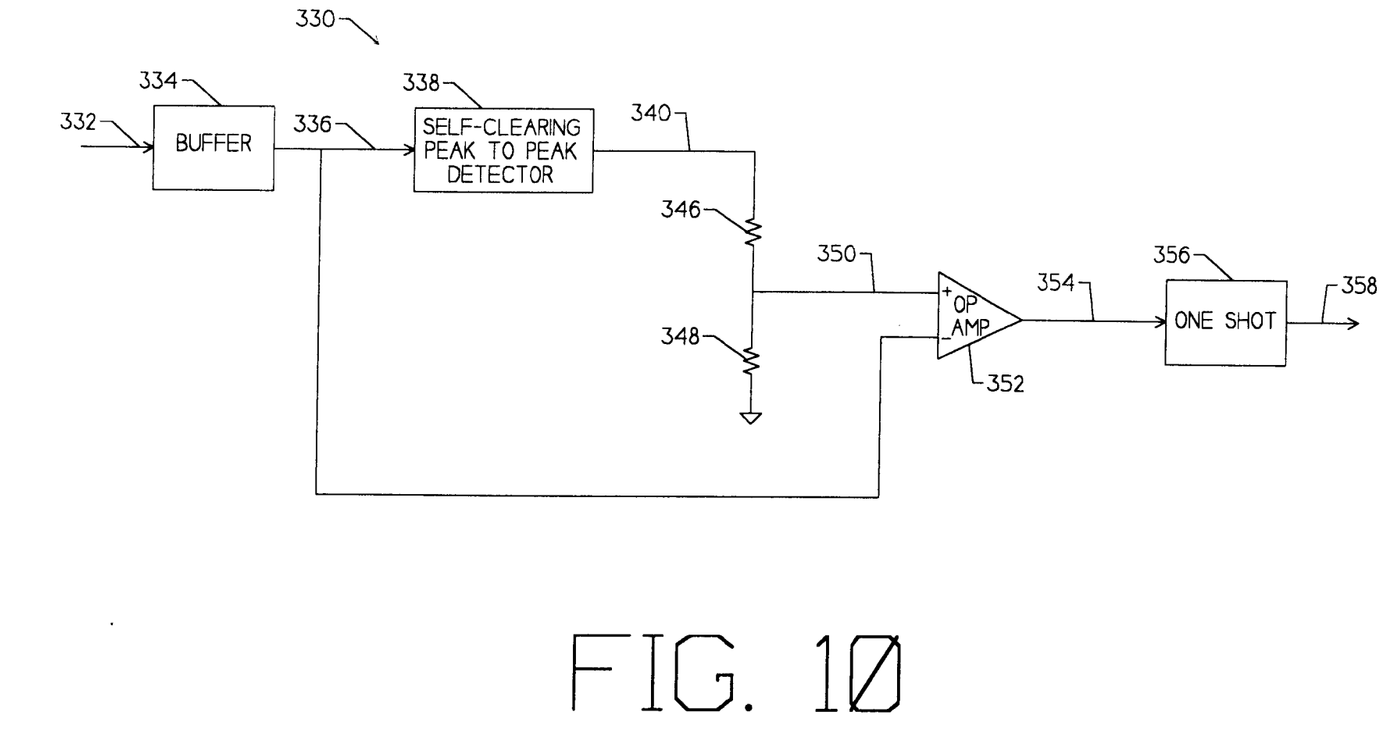
FIG. 10 is a block diagram showing an alternative embodiment of the present invention.

FIG. 10 is a block diagram showing an alternative embodiment of the present invention. The alternative embodiment is shown generally at 330 and includes a buffer 334, a self-clearing peak to peak detector 338, an operational amplifier 352, and a one-shot 356. Buffer 334 provides the same functionality as buffer 44 of FIG. 2. Self-clearing peak to peak detector 338 is described in FIG. 9.

Electrical signal 10 is input at interface 332. Buffer 334 provides an output at 336 which is responsive to the input at 332. Buffer 334 may be a unity gain amplifier or may provide other signal conditioning, as discussed in FIGS. 2 and 3. Self-clearing peak to peak detector 338 provides an output responsive to the sum of the positive and negative going peaks of the input at 336. The output of self-clearing peak to peak detector 338 is provided at interface 340 to a voltage divider network consisting of resistor 346 and 348. The positive input of operational amplifier 352 is coupled via interface 350 to resistor 346 and 348. The negative input of operational amplifier 352 is coupled to the output of buffer 334 at interface 336. Operational amplifier 352 performs a comparison function and compares the voltage divided peak to peak input from resistors 346 and 348 to the output of buffer 334. Since the R-wave of electrical signal 10 will typically have a greater peak to peak amplitude than other portions of the electrocardiogram waveform, by setting the proper threshold detection level through the ratio of resistors 346 and 348, operational amplifier 352 can sense the occurrence of an R-wave, and provide an output at interface 354.

The output of operational amplifier 352 is coupled to one shot 356 via interface 354. One shot 356 may optionally be used to provide a digital pulse output at interface 358, where the digital pulse output has CMOS voltage levels.

Having thus described the preferred embodiments of the present invention, those of skill in the art will readily appreciate that the teachings found herein may be applied to yet other embodiments within the scope of the claims hereto attached.

What is claimed is:

1. An apparatus for detecting an electrical cardiac voltage signal, comprising:
   a. signal conditioner adapted to be coupled to the electrical cardiac voltage signal for providing a number of conditioned voltage signals; and
   b. signal combiner coupled to the signal conditioner for combining the number of conditioned voltage signals to provide a combined voltage signal being distinguishable from each one of the number of conditioned voltage signals wherein the signal conditioner is a differentiator which calculates a number of derivatives of the electrical cardiac voltage signal and provides each one of the number of derivatives as one of the number of conditioned voltage signals, each one of the number of conditioned voltage signals having a magnitude which corresponds to a different order derivative of the electrical cardiac voltage signal than every other one of the number of derivatives.

2. An apparatus according to claim 1 wherein the magnitude of each one of the number of conditioned voltage signals corresponds to a peak value of the corresponding one of the number of derivatives.

3. An apparatus according to claim 1 wherein the signal combiner combines the number of conditioned voltage signals algebraically to provide the combined voltage signal, the combined voltage signal having a magnitude which is distinguishable from a magnitude of each one of the number of conditioned voltage signals.

4. An apparatus according to claim 3 wherein the signal combiner is a multiplier which combines the number of conditioned voltage signals by multiplying the number of conditioned voltage signals together to produce a product voltage which corresponds to a product of the number of conditioned voltage signals, the product voltage having a magnitude which is greater than a magnitude of any one of the number of conditioned voltage signals.

5. An apparatus according to claim 1 wherein the magnitude of each one of the number of conditioned voltage signals corresponds to a fraction of the peak value of the corresponding one of the number of derivatives.

6. An apparatus according to claim 1 wherein one of the number of derivatives of the electrical cardiac voltage signal is a zero order derivative of the electrical cardiac voltage signal.

7. An apparatus according to claim 1 wherein one of the number of derivatives of the electrical cardiac voltage signal is a first order derivative of the electrical cardiac voltage signal.

8. An apparatus according to claim 1 wherein one of the number of derivatives of the electrical cardiac voltage signal is a second order derivative of the electrical cardiac voltage signal.

9. An apparatus according to claim 1 wherein the electrical cardiac voltage signal is an R-wave.

10. An apparatus for detecting an electrical cardiac signal, comprising:
    a. differentiator means adapted to be coupled to the cardiac signal for providing a number of voltage values, each one of the number of voltage values corresponding to a different order derivative of the cardiac signal than every other one of the number of voltage values; and
    b. algebraic means coupled to the differentiator means for performing one or more operations on the number of voltage values to produce a result which has a greater magnitude than any one of the number of voltage values.

11. An apparatus according to claim 10 wherein the one or more operations are one or more multiplication operations and the result is a product of the number of voltage values.

12. An apparatus according to claim 10 wherein at least one of the number of voltage values corresponds to a zero order derivative of the cardiac signal.

13. An apparatus according to claim 12 wherein the at least one of the number of voltage value has a magnitude which corresponds to a peak value of the zero order derivative of the cardiac signal.

14. An apparatus according to claim 10 wherein at least one of the number of voltage values corresponds to a first order derivative of the cardiac signal.

15. An apparatus according to claim 14 wherein the at least one of the number of voltage values has a magnitude which corresponds to a peak value of the first order derivative of the cardiac signal.

16. An apparatus according to claim 10 wherein at least one of the number of voltage values corresponds to a second order derivative of the cardiac signal.

17. An apparatus according to claim 16 wherein the at least one of the number of voltage values has a magnitude which corresponds to a peak value of the second order derivative of the cardiac signal.

18. An apparatus according to claim 10 wherein the cardiac signal is an R-wave.

19. A sensing system for detecting an electrical cardiac signal, comprising:
    a. a differentiator circuit adapted to be operably coupled to the cardiac signal for providing a number of derivatives of the cardiac signal;
    b. a peak detector circuit operably coupled to an output of the differentiator circuit for providing a number of voltage values, each one of the number of voltage values corresponding to one on the number of derivatives of the cardiac signal; and
    c. an algebraic circuit operably coupled to an output of the peak detector circuit for performing one or more operations on the number of voltage values to produce a voltage result having a magnitude which is greater than any one of the number of voltage values.

20. A sensing system according to claim 19 wherein the algebraic circuit is a multiplier circuit and the one or more operations are one or more multiplication operations, the multiplier circuit multiplying the number of voltage values together to provide a product of the number of voltage values, the product of the number of voltage values having a magnitude which is greater than any one of the number of voltage values.

21. A sensing system according to claim 19 wherein at least one of the number of voltage values is a peak voltage value of a zero order derivative of the cardiac signal.

22. A sensing system according to claim 19 wherein at least one of the number of voltage values is a peak voltage value of a first order derivative of the cardiac signal.

23. A sensing system according to claim 19 wherein at least one of the number of voltage values is a peak voltage value of a second order derivative of the cardiac signal.

24. A sensing system according to claim 19 further comprising a fraction of peak detection circuit coupled to an output of the algebraic circuit for providing a voltage output in response to the voltage output of the algebraic circuit when the voltage output of the algebraic circuit has a magnitude which is greater than a predetermined level.

25. A sensing system according to claim 19 wherein the cardiac signal is an R-wave.

26. A sensing system for detecting an electrical cardiac signal, comprising:
    a. a first differentiator circuit adapted to be operably coupled to the cardiac signal for providing a first derivative of the cardiac signal;
    b. a second differentiator circuit operably coupled to an output of the first differentiator circuit for providing a second derivative of the cardiac signal;
    c. a first peak detector circuit adapted to be operably coupled to the cardiac signal for providing a peak voltage value to the cardiac signal;
    d. a second peak detector circuit operably coupled to the output of the first differentiator circuit for providing a peak voltage value of the first derivative of the cardiac signal;
    e. a third peak detector circuit operably coupled to an output of the second differentiator circuit for providing a peak voltage value of the second derivative of the cardiac signal; and
    f. a multiplier circuit operably coupled to an output of the first peak detector circuit, an output of the second peak detector circuit, and an output of the third peak detector circuit for multiplying the peak voltage values of the cardiac signal, the second derivative of the cardiac signal together to provide a voltage output which is greater in magnitude than the peak voltage value of the cardiac signal, the peak voltage value of the first derivative of the cardiac signal, or the peak voltage value of the second derivative of the cardiac signal.

27. A sensing system according to claim 26 further comprising a fraction of peak detection circuit coupled to the output of the multiplier circuit for providing a voltage output in response to the voltage output of the multiplier circuit when the voltage output of the multiplier circuit is greater than a predetermined level.

28. A sensing system according to claim 26 wherein the cardiac signal is an R-wave.

* * * * *